US008287654B2

(12) United States Patent
Shaffer

(10) Patent No.: US 8,287,654 B2
(45) Date of Patent: Oct. 16, 2012

(54) APPARATUS FOR CLEARING TUBING AND RELATED METHOD

(75) Inventor: Vance Shaffer, Beverly Hills, FL (US)

(73) Assignee: Gulf Medical Holdings, LLC, Beverly Hills, FL (US)

( * ) Notice: Subject to any disclaimer, the term of this patent is extended or adjusted under 35 U.S.C. 154(b) by 477 days.

(21) Appl. No.: 12/488,936

(22) Filed: Jun. 22, 2009

(65) Prior Publication Data

US 2009/0320879 A1    Dec. 31, 2009

Related U.S. Application Data

(63) Continuation-in-part of application No. 29/336,164, filed on Apr. 29, 2009, now Pat. No. Des. 624,645.

(60) Provisional application No. 61/076,289, filed on Jun. 27, 2008.

(51) Int. Cl.
*B08B 7/02* (2006.01)
*B08B 9/027* (2006.01)
(52) U.S. Cl. ......... 134/8; 134/16; 134/22.11; 15/104.08
(58) Field of Classification Search .................. 134/6, 8, 134/16; 251/6; 222/214, 102; 606/209; 15/104.08
See application file for complete search history.

(56) References Cited

U.S. PATENT DOCUMENTS

| | | | | |
|---|---|---|---|---|
| 3,194,452 A | * | 7/1965 | Sanderford | 222/407 |
| 3,648,701 A | * | 3/1972 | Botts | 606/209 |
| 3,881,635 A | * | 5/1975 | Canedo-Ramirez | 222/99 |
| 4,164,223 A | | 8/1979 | Munib | |
| 4,569,502 A | * | 2/1986 | Elliott | 251/8 |
| 5,071,102 A | * | 12/1991 | Gray | 251/4 |
| 5,881,916 A | | 3/1999 | Madjarac | |
| 6,641,260 B1 | * | 11/2003 | Avital | 351/41 |
| 7,309,055 B1 | | 12/2007 | Spiegel et al. | |
| 2004/0267305 A1 | | 12/2004 | Borgman | |
| 2005/0182432 A1 | * | 8/2005 | Fanton et al. | 606/168 |

OTHER PUBLICATIONS

International Search Report and Written Opinion (entire document), Int'l app. No. PCT/US2009/049154; dated Apr. 27, 2010.

* cited by examiner

*Primary Examiner* — Michael Kornakov
*Assistant Examiner* — Natasha Campbell
(74) *Attorney, Agent, or Firm* — Allen, Dyer, Doppelt, Milbrath & Gilchrist, P.A.

(57) ABSTRACT

An apparatus for clearing tubing includes a grip assembly connected to the pair of rollers. The grip assembly is operable to move the rollers to engage the tubing therebetween. The movement of the grip assembly is limited such that a minimum tubing gap between the rollers is equal to approximately twice a wall thickness of the tubing. The rollers are moved along the tubing to clear obstructions. The apparatus can also include a clamp assembly having one or more plates that limits movement of the grip assembly to bring the rollers no closer than the minimum tubing gap. Alternately, the grip assembly can include first and second shell halves movable between open and closed positions with a channel defined therebetween, and the rollers are mounted in the grip assembly.

14 Claims, 7 Drawing Sheets

APPARATUS FOR CLEARING TUBING AND RELATED METHOD

CROSS-REFERENCE TO RELATED APPLICATIONS

This application is a continuation-in-part of U.S. application Ser. No. 29/336,164, filed on Apr. 29, 2009, and claims the benefit of U.S. Provisional Application Ser. No. 61/076,289, filed on Jun. 27, 2008, the contents of which applications are hereby incorporated by reference in their entirety.

The present invention relates to the clearing of tubing, and more particularly, to devices for clearing surgical tubing.

BACKGROUND OF THE INVENTION

Tubing is employed as a fluid conduit in numerous applications. For example, after many invasive medical procedures, excessive fluid can build up in around affected tissues. This fluid build-up can cause discomfort, lead to infection and delay healing. Consequently, drains are inserted to collect fluid. Tubing, connected to the drains, carry the fluid away from the body.

However, in this and other applications, the tubing can become blocked due to factors such as the viscosity of the fluid and the presence of solid or semi-solid elements within the tubing. To prevent the blockages or clear them before excessive fluid can occur, the tubing must be cleared periodically. Most commonly, clearing tubing is done by hand, with the tubing being squeezed between the fingers along its length.

Hand clearing of tubing can be excessively time consuming. The time requirement is multiplied if multiple tubes must be cleared, as is often the case following many surgical procedures. Given the notoriously high workloads of hospital personnel, tubing is often inadequately or insufficiently cleared.

Additionally, repeatedly squeezing and pulling the tubing by hand stretches the tubing, sometimes to almost twice its original length. The stretched tubing becomes a greater nuisance for the patient and for other hospital personnel that must work around the patient.

Various devices have been proposed to facilitate the clearing of tubing. However, many of these devices are awkward or cumbersome to use. Additionally, the use of such devices still results in the pulling and stretching of the tubing.

SUMMARY OF THE INVENTION

Based on the foregoing, it is an object of the present invention to provide an improved apparatus and method for clearing tubing. According to the present invention, an apparatus for clearing tubing includes a pair of rollers, and a grip assembly connected to the pair of rollers. The grip assembly is operable to move the rollers to engage the tubing therebetween. The movement of the grip assembly is limited such that a minimum tubing gap between the rollers is equal to approximately twice a wall thickness of the tubing.

According to one embodiment of the present invention, the rollers are connected to the grip assembly by a clamp assembly, the clamp assembly including at least one plate having a pair of openings defined therein limiting the movement of the grip assembly.

According to another embodiment of the present invention, the grip assembly includes first and second shell halves movable between open and closed positions with a channel defined therebetween, and the rollers are mounted in the grip assembly.

According to an aspect of the present invention, the grip assembly and plurality of rollers are connected in an integral injection molded plastic web, such that the grip assembly and rollers can be separately removed therefrom and assembled into the apparatus for clearing tubing.

According to a method aspect of the present invention, a method of clearing tubing includes arranging the tubing between a pair of opposed rollers, bringing the rollers together to a distance of approximately two times a wall thickness of the tubing, and moving the rollers along the tubing.

These and other objects, aspects and advantages of the present invention will be better understood in view of the following detailed description of preferred embodiments.

DETAILED DESCRIPTION OF PREFERRED EMBODIMENTS

Figure 1:
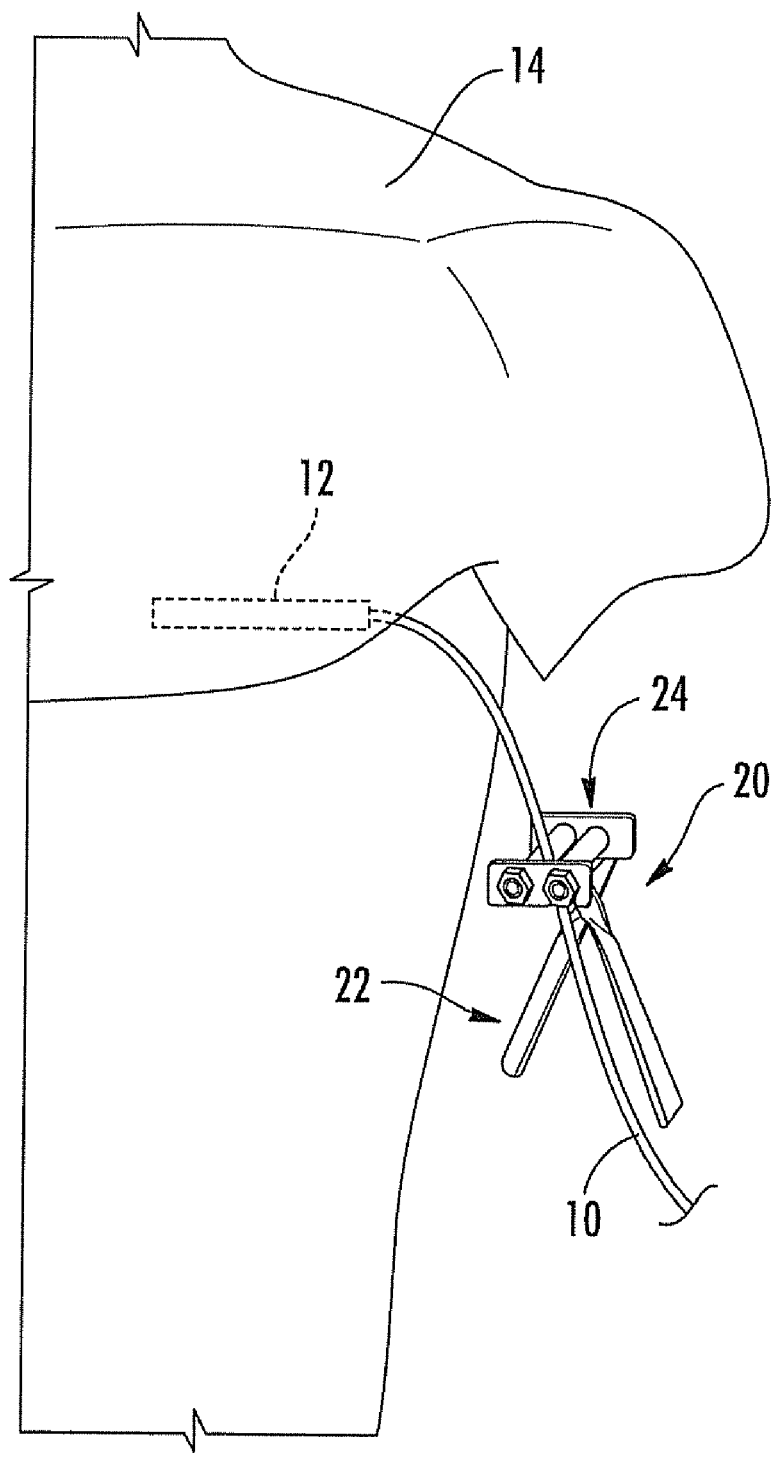
FIG. 1 is a schematic view of a body having tubing extending therefrom, and an apparatus for clearing tubing, according to an embodiment of the present invention.

Referring to FIG. 1, surgical tubing 10 extends from a drain 12 inserted within a body 14. An apparatus 20 for clearing tubing includes, according to an embodiment of the present invention, a grip assembly 22 facilitating gripping of the apparatus 20 by a user and a clamp assembly 24 for slidably engaging the tubing 10.

Figure 2:
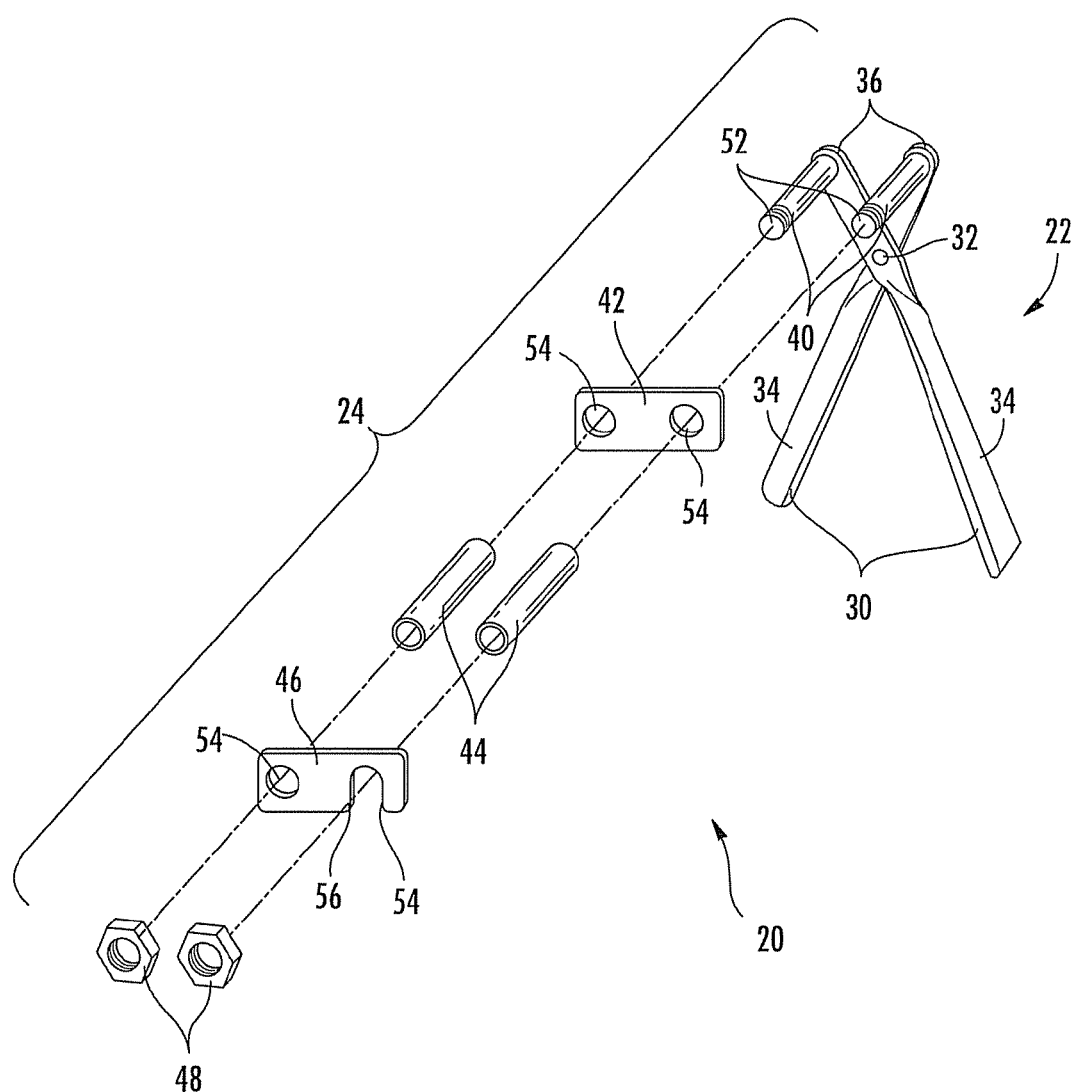
FIG. 2 is a partially exploded view of the apparatus of FIG. 1, showing details of a grip assembly and clamp assembly.

Referring to FIG. 2, the grip assembly 22 includes legs 30 connected by a pivot 32, such that bringing together and separating the first leg portions 34 results in a corresponding motion in the second leg portions 36.

The clamp assembly 24 includes arms 40 extending from second leg portions 36, and a first plate 42, rollers 44, a second plate 46 and retention elements 48 disposed about the arms 40. The arms 40 are connected to the second leg portions 36 such that bringing together and separating the second leg portions 36 results in a corresponding motion in the arms 40.

The arms 40 are advantageously formed from posts with threading on at least distal ends 52 thereof. The rollers 44 are advantageously formed from tubes having an inner diameter sufficient to fit around the arms 40 and allow rotation of the rollers 44 relative to the arms 40.

The first and second plates 42, 46 have a plurality of openings 54 defined therein. Advantageously, at least one of the openings 54 in the second plate 46 extends to an edge 56 thereof, allowing the second plate 46 to be selectively pivoted on and off one of the arms 36.

The retention elements 48 are advantageously formed as nuts that are threadable onto distal ends 52 of respective arms 40. With the retention elements 48 in place, the first and second plates 42, 46 and the rollers 44 are prevented from sliding off the arms 40.

Figure 3:
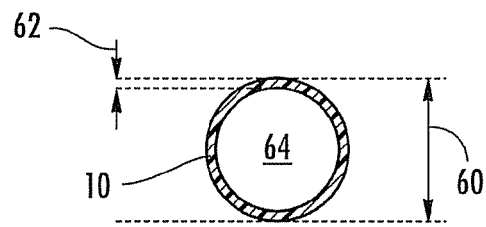
FIG. 3 is a sectional view of the tubing of FIG. 1.
Figure 4:
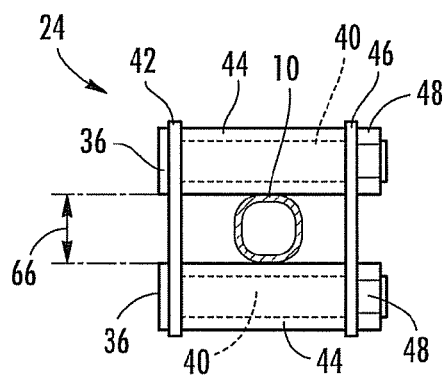
FIG. 4 is an schematic end view of the clamp assembly of FIG. 2 in an open configuration, with hidden components in broken lines.
Figure 5:
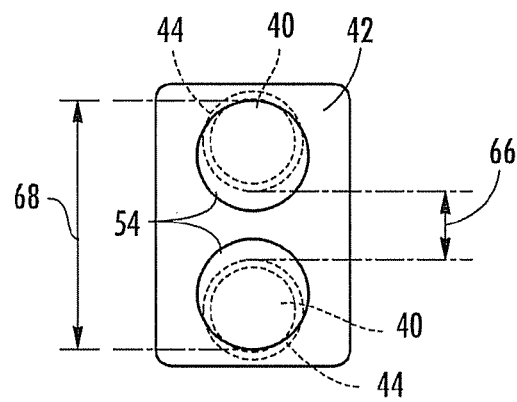
FIG. 5 is a view of a plate of the clamp assembly of FIG. 2, with components in the configuration of FIG. 4 in broken lines.
Figure 6:
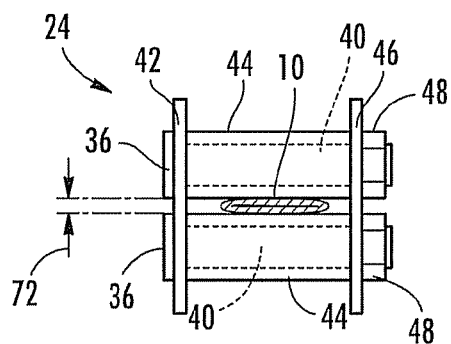
FIG. 6 is an schematic end view of the clamp assembly of FIG. 2 in a closed configuration, with hidden components in broken lines.
Figure 7:
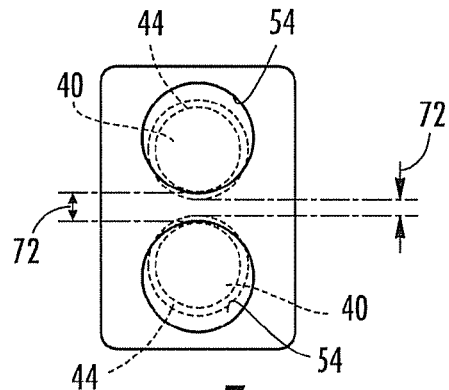
FIG. 7 is a view of a plate of the clamp assembly of FIG. 2, with components in the configuration of FIG. 6 in broken lines.

With reference to FIGS. 3-7, the alignment and dimensioning of the openings 54 with respect to the arms 36 and rollers 44 will be explained in greater detail. Except for the opening 54 extending to an edge 56 of the second plate 46, the alignment and dimensioning of the openings 54 of the first and second plates 42 are substantially the same. For expediency, only the first plate 42 is shown in FIGS. 5 and 7.

Referring to FIG. 3, tubing 10 has an outer diameter 60 and a wall thickness 62. In cross-section, the tubing defines an area 64. In FIG. 3, the tubing 10 is shown in its relaxed state. Referring to FIGS. 4 and 5, the arms 40 and rollers 44 are separable only to a maximum tubing gap 66. Distal edges of openings 54 are separated by a distance 68, limiting the separation of arms 40 and rollers 44, establishing the maximum tubing gap 66. Advantageously, the maximum tubing gap 66 is slightly less than the outer diameter 60 (see FIG. 3) of the tubing 10, inhibiting slipping between the tubing and the clamping assembly 24 when the tubing 10 is initially inserted between the arms 40 and rollers 44.

Referring to FIGS. 6 and 7, the arms 40 and rollers 44 can be brought together only to a minimum tubing gap 72. Proximal edges of openings 54 are separated by a distance 74, limiting the distance to which arms 40 and rollers 44 can be brought together, establishing the minimum tubing gap 72. Advantageously, the minimum tubing gap 72 is approximately equal to two times the wall thickness 62 (see FIG. 3) of the tubing 10.

With the minimum tubing gap 72 set to approximately two times the wall thickness 62, the area 64 (see FIG. 3) will be substantially eliminated. Thus, fluids or solids within the tubing 10 will be effectively forced in the travel direction of the apparatus 20, while compression of a substantial portion of the tubing wall below the wall thickness 62 is essentially avoided. Tubing stretch following repeated use of the apparatus 20 is correspondingly minimized.

In operation, referring to FIG. 2, the clamp assembly 24 of the apparatus 20 is assembled by sliding the first plate 42, rollers 44 and second plate 46 over the arms 40. These components are then secured in place by the retention elements 48. The second plate 46 is pivoted about one of the arms 40 and the grip assembly 22 is operated to separate the arms 40, establishing the maximum tubing gap 66 (see FIGS. 4 and 5) to allow the tubing 10 to be inserted between the rollers 44.

The second plate 46 is pivoted back into place to retain the tubing in place between the rollers 44 and first and second plates 42, 46. The grip assembly 22 is operated to bring the arms 40 together, establishing the minimum tubing gap 72 (see FIGS. 6 and 7) and pressing the tubing between the rollers 44. The apparatus 20 is then moved along the tubing 10 to clear fluids and solids therein.

Those skilled in the art will appreciate that, while the foregoing embodiment is exemplary of many features and aspects of the present invention, the present invention is not necessarily limited to such an embodiment. Instead, various modifications and adaptations to particular circumstances are possible within the scope of the present invention.

For instance, any suitable material, or combination of materials, can be selected for forming the various components of the apparatus of the present invention. Preferably, materials are selected to have durability and rigidity sufficient for a desired application of the apparatus. Also, for many medical applications, materials that are easily sterilized are also desirable. For example, for an apparatus intended for single or limited use, and then disposal, the various components can be formed from injected molded plastics.

The grip assembly 22 shown herein resembles a pliers-type assembly with the pivot 32 between first and second leg portions 34, 36 of legs 30. It will be appreciated that other grip assemblies can be used in connection with the present invention. For instance, the bringing together and separating of second leg portions is achievable with pivots located at different points along legs 30, as well as with legs 30 that are not pivotally connected. The terms "grip assembly" and "leg" do not necessarily imply structures of any particular length or dimensions, and an apparatus 20 with a grip assembly 22 that is directly connected to the rollers 44 is possible within the scope of the present invention.

In general, the dimensions of the grip assembly and clamp assembly, and components thereof, can be selected as suitable for a particular application or range of applications. For example, components of the clamp assembly can be dimensioned to establish maximum and minimum tubing gaps to correspond to given surgical tubing dimensions.

Figure 8:
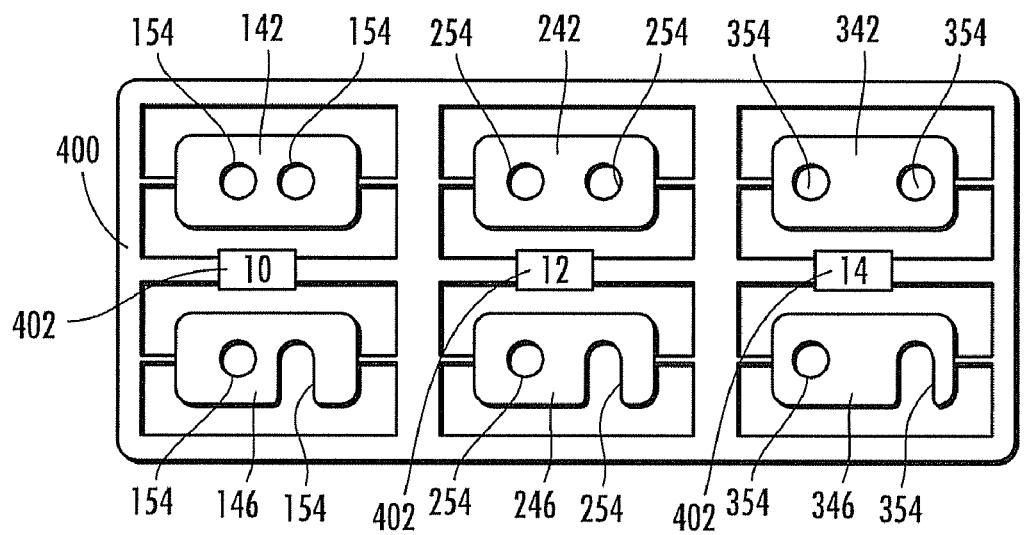
FIG. 8 is a top plan view of web of plates for use in connection with the clamp assembly of FIG. 2, according to an aspect of the present invention.

The present invention can be adapted to selectively accommodate a range of tubing dimensions. Referring to FIG. 8, a plurality of first plates 142, 242, 342 and second plates 146, 246, 346 have a plurality of openings 154, 254, 354 with varying spacing to establish different maximum and minimum tubing gaps. Advantageously, the plates 142-342, 146-346 can be integrally formed in a web 400, for example, by injection molding. Individual plates 142-342, 146-346 can then be easily snapped out of the web for use. Indicia 402 can be included in the web to indicate the tubing size corresponding to the different plates.

Figure 9:
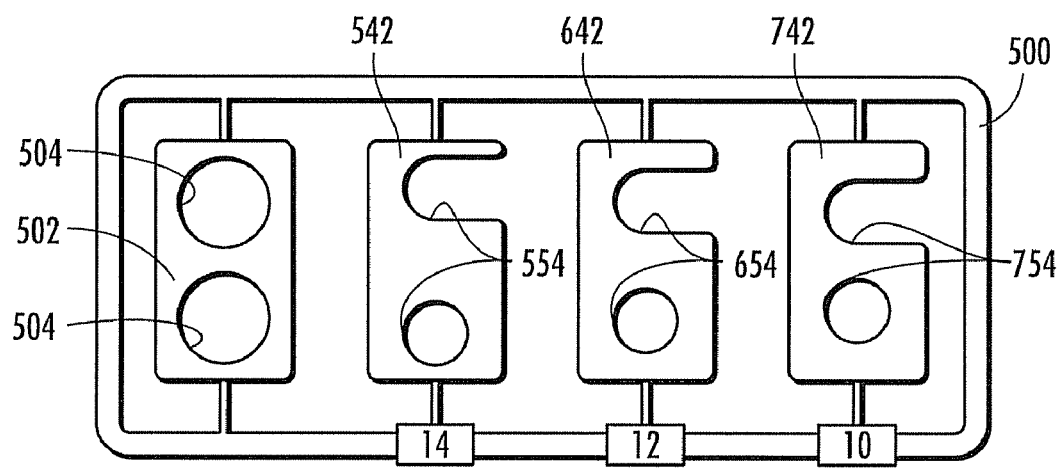
FIG. 9 is a top plan view of a web of plates for use in connection with the clamp assembly of FIG. 2, according to another aspect of the present invention.

Configurations are also possible where it is not necessary to interchange both first and second plates. Referring to FIG. 9, a web 500 includes a second plate 502 and a plurality of first plates 542, 642, 742. Openings 504 on the second plate 502 are large enough to accommodate the largest maximum tubing gap and smallest minimum tubing gap established by the openings 554, 654, 754 in the first plates 542, 642, 742. In such a configuration, the first plates 542, 642, 742 set the maximum and minimum tubing gaps and the second plate 502 assists in retaining the tubing between the rollers 44.

It will also be appreciated that the present invention is not necessarily limited to clamp assemblies in which both maximum and minimum tubing gaps are established. For instance, an apparatus having a clamp assembly only establishing a minimum tubing gap is possible within the scope of the present invention. Additionally, the present invention is not necessarily limited to clamp assemblies with first and second plates. For instance, clamp assemblies establishing a maximum or minimum tubing gap with a single plate are possible within the scope of the present invention. Also, the term "plate" does not necessarily denote a particular shape or geometry.

Figure 10:
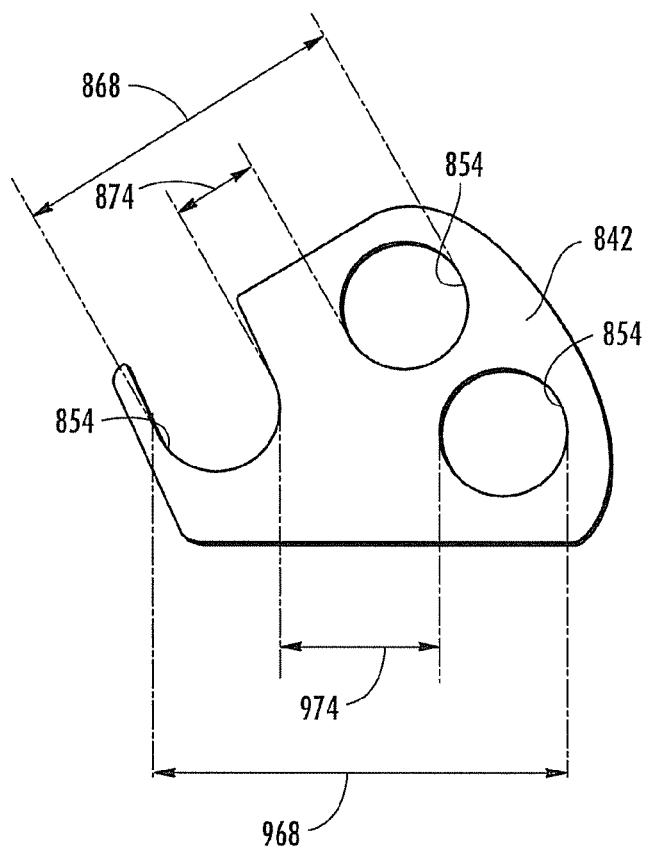
FIGS. 10-12 are alternate plate configurations, according to further aspects of the present invention.

Referring to FIG. 10, a plate 842 has a plurality of openings 854, allowing the plate 842 to be used to set different maximum and minimum tubing gaps. For instance, two of the openings 854 have distal edges and proximal edges separated by respective distances 868, 874. Another two of the openings have distal edges and proximal edges separated by greater respective distances 968, 974.

Figure 11:
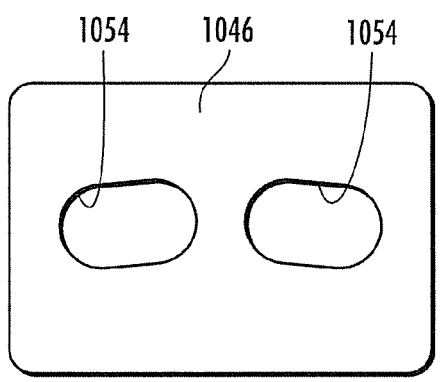
Figure 12:
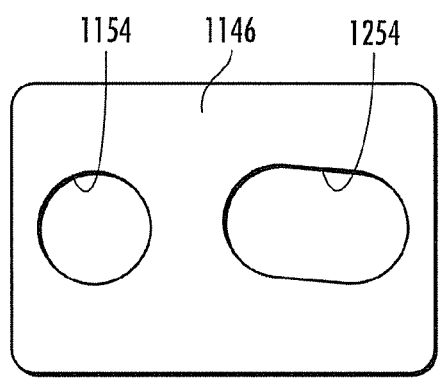

Additionally, the present invention is not necessarily limited to plates having round or semicircular openings. For instance, referring to FIG. 11, a plate 1046 has oblong openings 1054. Similarly, openings that are the same size are also not necessarily required. For example, referring to FIG. 12, a plate 1146 has a circular opening 154 and an oblong opening 1254.

Also, the length of rollers 44 can be selected based on given tubing dimensions. Advantageously, the rollers 44 should be at least long enough to accommodate tubing when pressed to the minimum tubing gap. While multiple rollers 44 could be supplied in a kit with other components of the apparatus 20, rollers having a length of approximately ⅜ inch have been found to readily accommodate most commonly used surgical tubing sizes. Additionally, clamp assemblies without separate rollers 44, for instance where one or more arms 40 are rotatably mounted, or fixedly mounted. In such a configuration, the tubing gaps would be defined by the distances between the arms or equivalent elements.

Also, different retention elements 48 can be employed, other than threaded fasteners. For example, snap fit fasteners can be employed. Alternately, retention elements can be omitted or their function integrated into one or more other elements.

Figure 13:
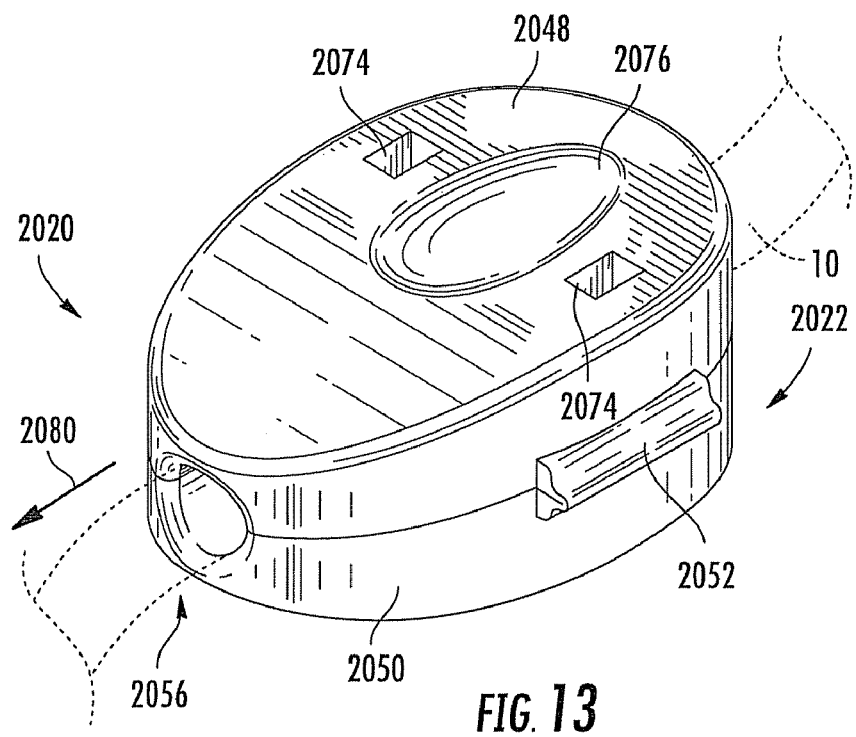
FIG. 13 is a perspective view of an apparatus for clearing tubing, according to another embodiment of the present invention.
Figure 14:
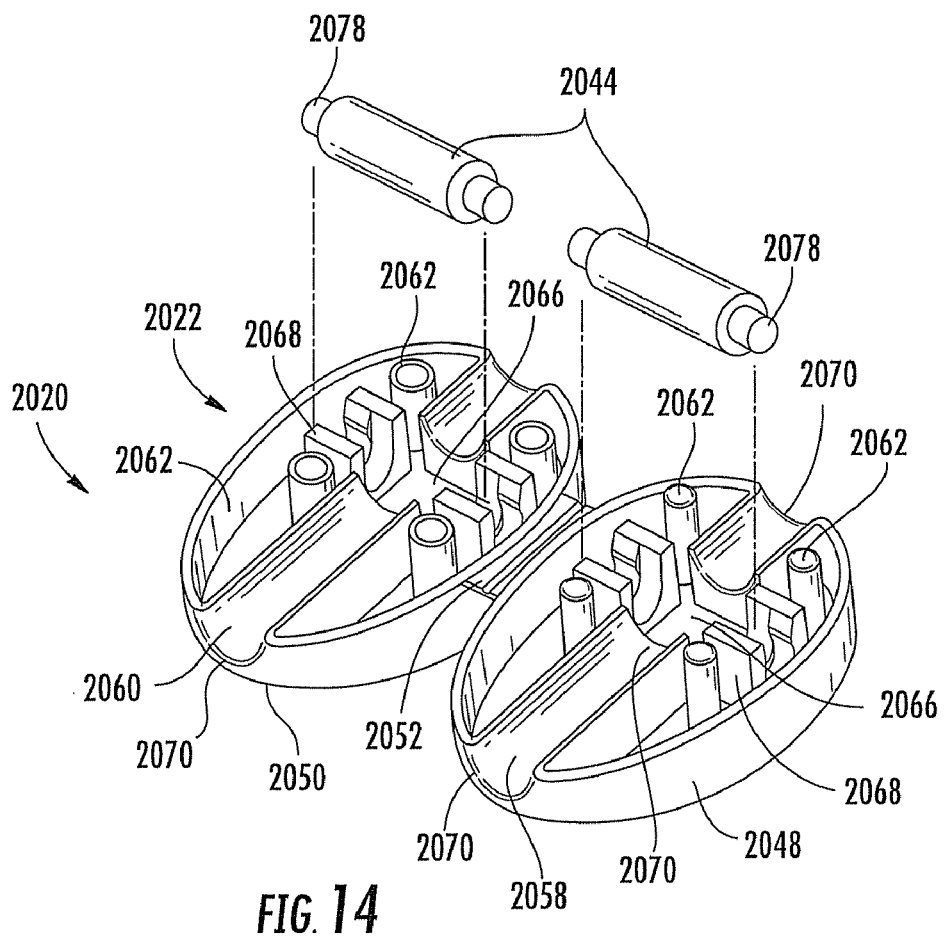
FIG. 14 is a partially exploded view of the apparatus of FIG. 13, in an open position.

Additionally, according to a further another embodiment of the present invention, referring to FIGS. 13 and 14, an apparatus 2020 for clearing tubing includes a grip assembly 2022 with a pair of rollers 2044 internal thereto. Like the apparatus 20, the apparatus 2020 is displaceable along the tubing 10 to clear obstructions therefrom.

The grip assembly 2022 is formed from first and second shell halves 2048, 2050 connected by a hinge 2052. A channel 2056, extending through the grip assembly 2022, is defined by opposed channel halves 2058, 2060 with the first and second shell halves 2048, 2050 closed.

Complementary engagement elements 2062, such as solid and hollow posts, are also formed in the first and second shell halves 2048, 2050 to ensure proper alignment of the shell halves 2048, 2050 when folded together. Gaps 2066 are defined in each of the channel halves 2058, 2060 to accommodate the rollers 2044.

Roller mounting brackets 2068 are formed in the first and second shell halves 2048, 2050 on opposite sides of each the gaps 2066. The channel halves 2058, 2060 have rounded edges 2070 on both sides of each gap 2066 and at terminal ends of the channel 2056. Penetrations 2074, aligned with the roller mounting brackets 2068, extend through the first and second shell halves 2048, 2050. Grip recesses 2076 are formed on outer surfaces of the first and second shell halves 2048, 2050, preferably with approximately orthogonal major axes (see FIG. 16).

The rollers 2044 are preferably also injection molded from plastic. Reduced diameter portions 2078 are formed on each end of the rollers 2044. The reduced diameter portions 2078 are dimensioned to snap fit into the roller mounting brackets 2068, with the rollers 2044 rotatable relative to the mounting brackets 2068 when retained therein. The rollers 2044 are preferably removable and replaceable. Insertion of a tool tip (not shown) through the penetrations 2072 can be used to facilitate removal.

Figure 15:
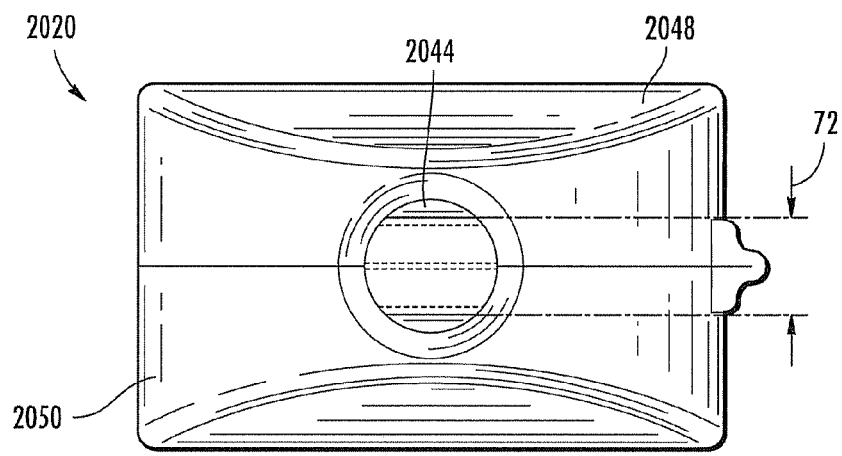
FIG. 15 is a front view of the apparatus of FIG. 13.

In operation, referring to FIGS. 13-15, the rollers 2044 are snap fit into the brackets 2068. With the shell halves 2048, 2050 open, the apparatus 2020 is placed along tubing 10 such that the tubing extends along one of the channel halves 2058, 2060. The grip assembly 2022 is closed, forming the channel 2056 which surrounds the tubing 10 and bringing the rollers 2044 together to a minimum tubing gap 72, equal to approximately two times the wall thickness of the tubing 10.

The apparatus 2020 is preferably gripped between the fingers, with the thumb on the recess 2076 of the first shell halve 2048 and the forefinger on the recess 2076 of the second shell halve 2050. The apparatus 2020 is then displaced in the direction of arrow 2080, which corresponds with a narrower end of the grip assembly 2022, to clear obstructions from the tubing 10.

Figure 16:
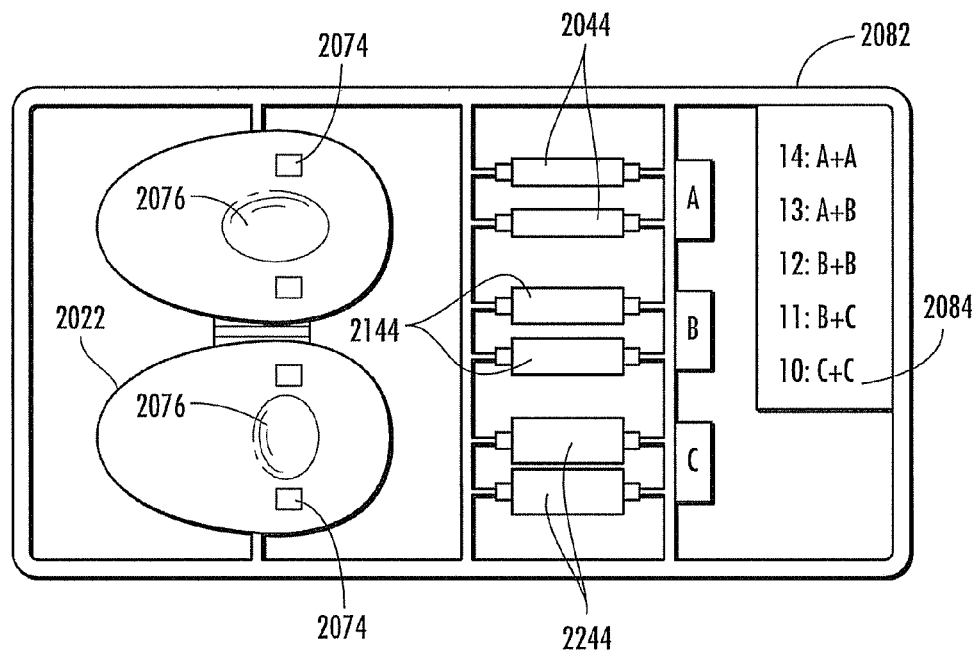
FIG. 16 is a top plan view of a web including the apparatus of FIG. 13.

Referring to FIG. 16 the grip assembly 2022 (including all internal components) and the rollers 2044 can be advantageously formed as part of a single, injection molded plastic web 2082. The grip assembly 2022 and rollers 2044 can be separately snapped out of the web 2082 and assembled. Different diameter rollers 2144, 2244, having the same diameter end portions for compatibility with the brackets 2068, can also be formed in the web 2082, allowing different minimum tubing gaps to be set to accommodate tubing of different diameters. Preferably, a key 2084 is also formed in the web, indicating which combination of rollers, 2044, 2144, 2244 should be used to achieve the appropriate minimum tubing gap for different tubing sizes.

It will be appreciated that the apparatus 2020 offers many of the same benefits of the apparatus 20 in an extremely compact, single and lightweight package, that can be quickly and easily assembled and used. Additionally, the apparatus 2020 can be readily included in sterilized, pre-packed surgical drain kits and the like.

It will also appreciated that the either of the apparatus 20, 2020 can be moved to either clear tubing away from the body, for example, as in a drain, or towards the body, for example, as in a feeding tube. Moreover, the apparatus of the present invention can be employed to clear tubing in non-medical applications.

The foregoing examples are not an exhaustive list of modifications and adaptations. Rather, those skilled in the art will appreciate that these and other changes are possible within the scope of the invention herein shown and described, and of the appended claims.

What is claimed is:

1. An apparatus for clearing surgical tubing, the apparatus comprising:
  a pair of rollers; and
  a grip assembly connected to the pair of rollers;
  wherein the grip assembly is operable to move the rollers to engage the tubing therebetween, the movement of the rollers being limited by the grip assembly such that a minimum tubing gap between the rollers is equal to approximately twice an uncompressed wall thickness of the tubing such that the tubing is closed but the tubing wall is not squeezed to less than the uncompressed wall thickness, the grip assembly being further operable to slide along the tubing with the rollers; and wherein the grip assembly includes first and second shell halves movable between open and closed positions with a channel defined therebetween, and the rollers are mounted in the grip assembly, engagement between the first and second shell halves in the closed position preventing bringing the rollers together to less than the minimum tubing gap.

2. The apparatus of claim 1, wherein at least one of the rollers is rotatably mounted.

3. The apparatus of claim 1, wherein the each shell half includes a pair of roller mounting brackets, and the rollers include reduced diameter end portions that snap fit into the roller mounting brackets.

4. The apparatus of claim 1, wherein each shell half includes a channel half defined therein, the channel halves defining the channel with the shell halves in the closed position.

5. The apparatus of claim 4, wherein a gap is formed in each channel half and each shell half includes a pair of roller mounting brackets on opposite sides of the gap.

6. The apparatus of claim 4, wherein the channel halves include rounded edges at respective ends thereof.

7. The apparatus of claim 1, wherein the first and second shell halves have complementary engagement elements.

8. The apparatus of claim 1, wherein the first and second shell halves are connected by a hinge.

9. A method of clearing tubing, the method comprising:
arranging the tubing between a pair of opposed rollers;
bringing the rollers together to a distance of approximately two times an uncompressed wall thickness of the tubing such that the tubing is closed but the tubing wall is not squeezed between the rollers to less than the uncompressed wall thickness; and
moving the rollers along the tubing; wherein bringing the rollers together includes operating a grip assembly, the grip assembly being limited such that the rollers cannot be brought together to more than the distance approximately two times the wall thickness of the tubing; and wherein the operating the grip assembly includes closing first and second shell halves having the rollers mounted therein, engagement between the shell halves when brought together effecting the limitation of roller movement.

10. A tube clearing apparatus for clearing surgical tubing having an uncompressed wall thickness, the tube clearing apparatus comprising:
a pair of rollers;
a grip assembly holding the pair of rollers such that the grip assembly and rollers can slide along the surgical tubing for the clearing thereof, the grip assembly including pair of shell halves movable between an open position, in which the surgical tubing can be placed therebetween, and a closed position, in which the rollers are brought into proximity on opposite sides of the surgical tubing, engagement between the shell halves in the closed position preventing bringing the rollers closer together than a minimum tubing gap therebetween, the minimum tubing gap being equal to approximately two times the uncompressed wall thickness of the surgical tubing such that the tubing is closed but the tubing wall is not squeezed between the rollers to less than the uncompressed wall thickness.

11. The apparatus of claim 10, wherein channel halves defined in each of the shell halves further define a tubing channel when the shell halves are in the closed position with openings at opposite ends thereof, the channel being divided into two portions, each portion leading from one of the openings to the rollers.

12. The apparatus of claim 10, wherein the shell halves are connected by a hinge.

13. The apparatus of claim 12, wherein the hinge and shell halves are integrally formed as a single unit.

14. The apparatus of claim 10, further comprising the surgical tubing arranged between the rollers.

* * * * *